United States Patent

Sultan

[11] Patent Number: 6,135,945
[45] Date of Patent: Oct. 24, 2000

[54] ANTI-INCONTINENCE DEVICE

[76] Inventor: Hashem Sultan, 8455 Island Pines Pl., Mainville, Ohio 45039

[21] Appl. No.: 08/905,670

[22] Filed: Aug. 4, 1997

[51] Int. Cl.$^7$ .................................................. A61F 2/00
[52] U.S. Cl. .................................. 600/30; 128/DIG. 25; 607/40
[58] Field of Search .................. 600/29–31; 607/40–41; 128/DIG. 25, 885

[56] References Cited

U.S. PATENT DOCUMENTS

| | | |
|---|---|---|
| 5,013,292 | 5/1991 | Lemay . |
| 5,019,032 | 5/1991 | Robertson . |
| 5,082,006 | 1/1992 | Jonasson . |
| 5,112,344 | 5/1992 | Petros . |
| 5,417,226 | 5/1995 | Juma . |
| 5,518,504 | 5/1996 | Polyak . |
| 5,520,606 | 5/1996 | Schoolman et al. . |
| 5,611,768 | 3/1997 | Tutrone . |

Primary Examiner—Lee Cohen
Assistant Examiner—Roy Gibson
Attorney, Agent, or Firm—Wood, Herron & Evans LLP

[57] ABSTRACT

An apparatus for preventing uncontrolled discharge of urinary fluid from a patient urethra includes a pressure sensor operable for sensing intra-abdominal pressure when implanted in a patient and operable for generating a pressure signal in response to said sensed pressure, An actuating device is operably coupled to the pressure sensor and is responsive for generating an electrical signal in response to the pressure signal. A controller is operably coupled to the actuating device and configured for engaging a urethra to selectively compress the urethra and prevent incontinence. The controller includes a plate adapted to be positioned on one side of the urethra and an element adapted to be positioned on another side of the urethra and is operable for varying the distance between the element and the plate in response to said electrical signal to compress the urethra therebetween so that incontinence is prevented when intra-abdominal pressure is experienced by a patient.

19 Claims, 6 Drawing Sheets

ANTI-INCONTINENCE DEVICE

BACKGROUND

1. Field of Invention

This invention relates generally to implantable medical devices, and more specifically to a device used for treatment of stress incontinence

2. Description of Prior Art

Incontinence is a major health problem in the United States and accounts for approximately $ 10 billions for our annual health care costs. It is estimated that over 10 million individuals suffer from urinary incontinence, 60–70% of which are females.

Although there are several types of female incontinence, stress incontinence or stress and urge incontinence is the most common. Stress incontinence is triggered by sudden tensing of the abdominal muscles which occurs during coughing, laughing, and certain physical activities. It is caused by abnormalities in the anatomy of the bladder outlet structures, the sphincter and the urethra.

This problem is most pronounced in the elderly female population due to prolapse of the uterus which distorts the geometry of the bladder neck resulting in a 30% incontinence rate in women over 60 years of age. This problem causes acute embarrassment and inhibits physical and social activity.

Many methods and devices for managing incontinence are currently available;

One of the available methods is the use of an artificial, inflatable urinary sphincter, generally comprises an inflatable cuff, a fluid reservoir and a pump. The artificial sphincter is surgically implanted so that the cuff surrounds the urethra and the pump is placed in an accessible location such as scrotum in male or labia majora in female. The cuff is normally filled with fluid so as to constrict the bulbar urethra and prevent the bladder from emptying. When the user wishes to empty his bladder, the pump is squeezed, which forces fluid out of the cuff and into the reservoir, thereby deflating the cuff and opening the urethra. Although relatively effective, the artificial inflatable urinary sphincter has some serious shortcomings. The main difficulty with such a sphincter is that the constant encircling pressure applied to the bulbar urethra results in unacceptable urethral erosion and scarring because the sphincter encircles the urethra and substantially restricts blood flow therein. After several years of use, such a sphincter may result in sever damage to the urethra.

U.S. Pat. No. 5,520,606 date May 28, 1996, describes an apparatus comprises an inflatable, urethra-compressing balloon having a tissue engaging surface positioned between the urethra on a side of the urethra opposite the pubic bone. A patient having the apparatus surgically implanted therein may selectively advance hydraulic fluid between the reservoir and the balloon so as to inflate or deflate the balloon and prevent or allow bladder emptying respectively.

Many procedures involving urethro-vesical elevation, have been devised over the years to cure stress incontinence. Some of those are described in U.S. Pat. No. 5,112,344 and U.S. Pat. No. 5,019,032.

A sling procedure is disclosed in U.S. Pat. No. 5,013,292 in which a method is described by implanting a sling-like anchoring device in the skin above the symphysis pubis to adjust the urethro vesical angle. An implantable sphincter system utilizing lifting means is described in U.S. Pat. No. 5,518,504 date May 21, 1996 in which an actuating device is operably connected to the lifting and lowering device, and a pump capable of being volitionally operated is in fluid communication with the actuating device to provide a pressurized flow of fluid into the actuating device.

Other devices disclosed in prior arts rely mainly on urethral occlusion; U.S. Pat. No. 5,090,424, U.S. Pat. No. 5,082,006, U.S. Pat. No. 5,417,226 date May 23, 1995.

Intra vaginal devices to compress the urethra are also described in many old patents and recently in U.S. Pat. No. 5,611,768.

Up to the present, there remains a need for an apparatus which maintain continence without damaging the tissue of the bladder, urethra, or surrounding areas. A need for a device that allow the maximum use of the normal remaining function of the urethral sphincter and to be activated spontaneously and only temporarily when it is needed (when the intra-abdominal pressure rises above a certain level that causes the incontinence), and deactivated spontaneously when it is not needed,

SUMMARY OF THE INVENTION

The current invention is an implantable device which enhances urethral sphincter closure only when intra-abdominal pressure rises above a certain value that causes incontinence. This is achieved by a pressure sensor implanted with the device in the abdominal cavity. The device is, therefor activated only with such activities as coughing, laughing, and other physical activities that increases intra- abdominal pressure. and remains deactivated when the intra-abdominal pressure is within the range that does not cause incontinence.

To permit bladder emptying, which needs straining and increasing intra-abdominal pressure, the patient can deactivate the device by either pushing a switch implanted under the skin, or by a remote control.

Four basic types of the device are disclosed in this application. All four types comprises four main parts; a pressure sensor, actuating device, controller device, and connectors between these devices.

The actuating device is implanted under the skin and is activated by signals received from a pressure sensor implanted in the abdominal cavity. A variable resistors included in the actuating device allow determining the intensity of the signal upon which the device is activated.

Deactivation of the device to permit emptying the bladder is achieved either manually by a switch implanted under the skin or by a remote control using radio frequency, infrared, ultrasound or any other means of telecommunication.

Type (A) and type (B) of the controller device comprises an electromagnetic bar located above the urethra and a basal plate located underneath the urethra. When activated, a magnetic field is created allowing the movement of the electromagnet bar into the basal plate and compressing the urethra in between. When the intrabdominal pressure falls to acceptable range, the electromagnet is switched off. The bar moves away from the basal plate by either a spring (type A) or by a compressible fluid or gas in barrels (type B).

The electromagnet circuit of type (C) is preferably included in the actuating device. When activated, an electromagnetic field is generated pulling a moving bar into a fixed plate, pushing a plunger of a barrel containing hydraulic fluid or gas. The barrel is connected to the controller device type (C) by a non-compliant tube, pushing a plunger which compresses the urethra against a basal plate.

Type (D) of the device has an actuating device similar in its components to type (A) and type (B), but differs in that its controller is a lead implanted into the wall of the urethral sphincter and causes electrical stimulation which enhances the contraction of the sphincter during the increase in the intra-abdominal pressure.

A large number of different types of devices can be made, using the same principles of the above devices, by changing the relation and position of the moving part to the fixed part of the device.

A method of placing the basal plate under the urethra, to reduce the risk of injuring the urethra or the vaginal wall, is also disclosed. An IV (intravenous) type catheter is passed between the urethra and the vaginal wall, and then a guiding wire is passed through the catheter. The catheter is then removed, and different sizes of dilators are passed over the wire until the space is large enough to allow the passage of the basal plate.

The other part of the controller is then fixed to the basal plate preferably by a click mechanism, but any means of fixation can be used The current invention offers several advantages over the prior devices:

- It is activated only when intra-abdomial pressure rises, which allows the maximum use of the remaining function of the urethral sphincter.
- Being activated only when intra-abdominal pressure rises, the compression of the urethra is only transient and minimal in duration which eliminates the risk of urethral damage caused by constant pressure in the prior devices.
- Optimal efficiency and reliability.
- A wide range of values of intra-abdominal pressure upon which the device is activated, therefore, allowing the device to work effectively in any degree of severity of the disease.
- No dissection around the urethra is required, therefore eliminating or reducing the risk of tissue injury.

REFERENCE NUMERALS IN DRAWINGS

1-Pressure sensor.
2-Transducer.
3-Variable resistor.
4-Selector of the resistor value.
5-Switch 1 turns on the device only when the signal of the pressure sensor exceeds the set value.
6-Switch 2 is to deactivate/activate the device by a remote control.
7-Switch 3 is located under the skin to manually deactivate/activate the device.
8-Receiver.
9-Transducer.
10-Power supply.
11-Basal plate.
12-Coiled wire.
13-Metal bar.
14-Cushion.
15-Electromagnetic bar.
16-Barrel
17-Plunger.
18-Spring.
19-Sliding bar.
20-A barrel leg.
21-an envelope or a frame of the device.
22-Compress able gas or liquid.
23-Stitches.
24-Non-friction sliding end.
25-Electromagnet bar.
26-Plunger.
27-Non-friction slider or wheels.
28-Fixed metal bar.
29-Barrel,
30-Non-compress able fluid or gas.
31-Non-compliant tube.
32-Barrel.
33-Plunger.
34-Spring.
35-Cushion.
36-Holder of the barrel.
37-Hole for the leg of the frame or envelope of the device (21).
38-Hole for the barrel leg (20)
39-Stimulator lead to the urethral sphincter.
40-Sling.
41-Cords.
42-Spring.
43-Stabilizer.

DETAILED DESCRIPTION OF THE PREFERRED EMBODIMENTS

The present invention is intended to be used in stress incontinence in both male and female. However, if indicated it can be used in all other types of incontinence.

Several types and forms of the device are disclosed in this application. They vary in the arrangement of the embodiments, but shares the general main features and the main spirit of the invention; mainly controlled closure of the urethra. Four main types of the invention; type A,B,C,D are discussed in details.

Generally, the device comprises five main parts:
1-pressure sensor; which senses the increase in intra-abdominal pressure,
2-Actuating device; which transform the signal received from the pressure sensor into electrical stimulation. It may also contain the necessary circuits to communicate with an external controller.
3-A manual switch; implanted under the skin to manually activate/deactivate the device.
4-A controller device; which execute the function of closing the urethra when the intra-abdominal pressure increases "control-closure".
5-Connection between these various devices with suitable connectors tunneled under the skin.

Figure 1:
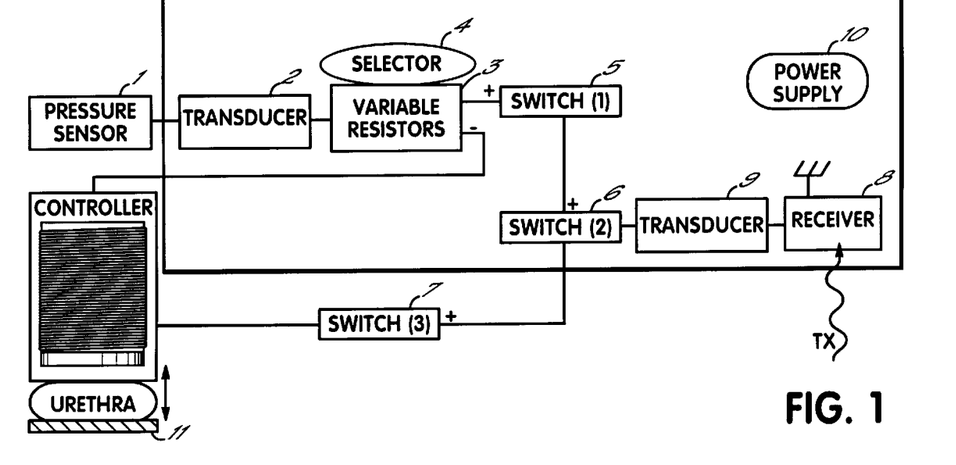
FIG. 1 is a schematic view of one embodiment of the invention.
Figures 8, 13A, 13B:
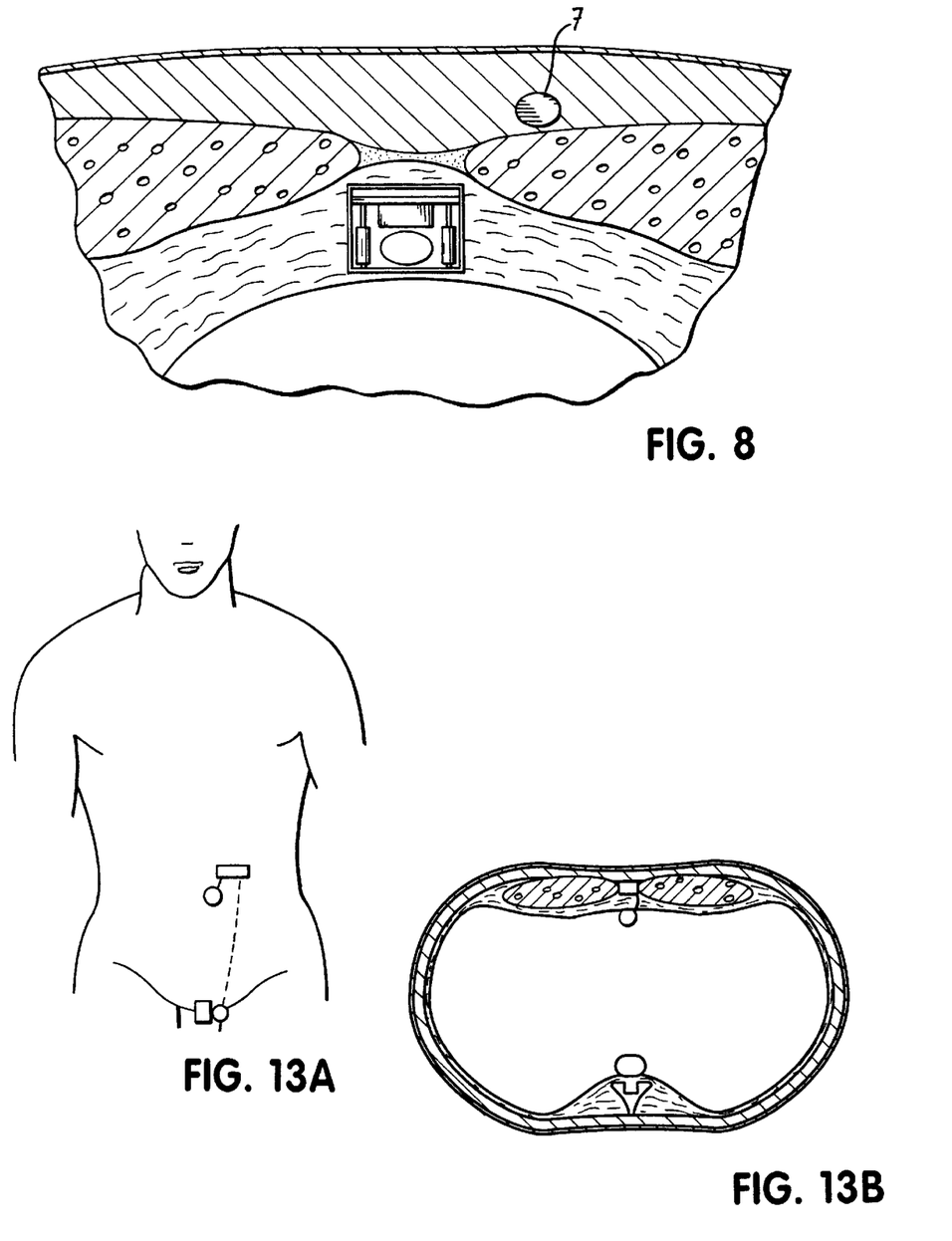
FIG. 8 is a cross-sectional view of a lower abdomen of a female indicating the environmental placement of the invention.
FIG. 13A is a front view of a person showing positioning of components of the invention.
FIG. 13B is a cross-sectional view of a person showing positioning of components of the invention.

FIG. 1 illustrates the preferred embodiments of the actuating device to controller type A,B. A pressure sensor (1) is implanted in the pelvis or the abdomen using the same incision used for implanting the actuating device which is implanted under the skin, FIG. 13.

The signal received from the sensor is transformed into electrical energy by a transducer (2). The current thus generated is passed through a variable resistors (3) the value of the resistance chosen determines the current output. The value of the resistance chosen for a particular patient correlates inversely with the severity of the incontinence.

The variable resistors and its selector dial (4) is not a necessary component of the device.

Figure 12:
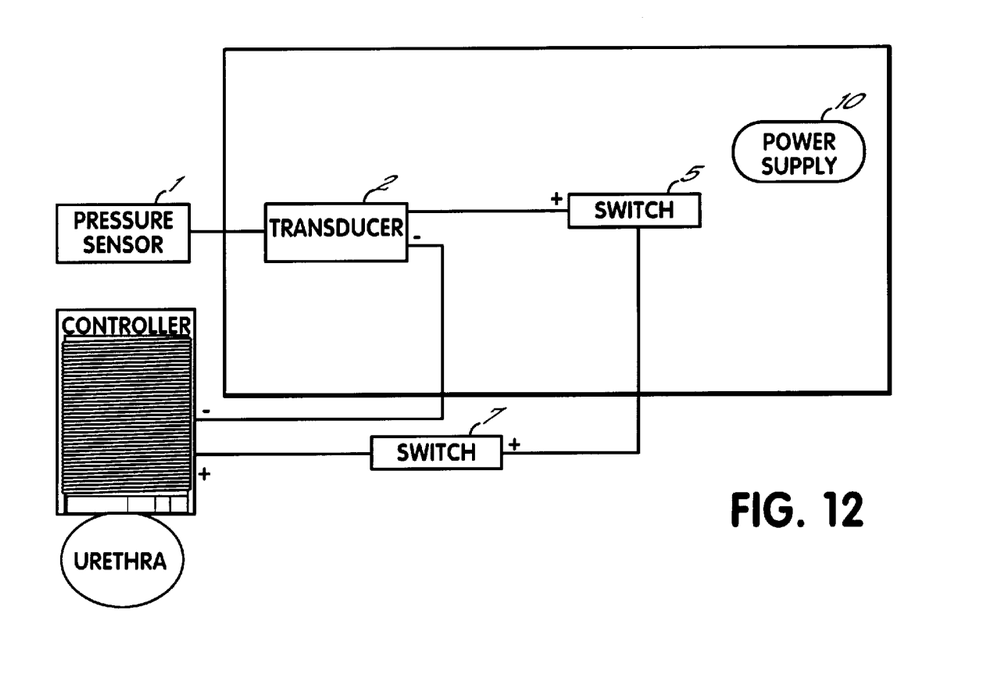
FIG. 12 is a schematic view of another embodiment of the invention.

The device can be manufactured either with different values of the resistance (very low, low, medium, high, very high, etc . . . ) or different values of sensitivity of the pressure sensor to the increase in intra-abdominal pressure with no resistance required in the device, This is the simplest form of the actuating device and is illustrated in FIG. 12. The more sever the disease, the higher the sensitivity of the sensor is required.

Therefor, in this option, the device with a particular sensitivity or resistance is chosen by the operator for a particular case according to the severity of the disease.

The disadvantage of this choice is that there will be a need to change the actuating device if the disease worsens with the progress of the underlying disease. However, the advantage is very obvious, namely reducing the cost of the device and simplicity In all cases, If the intensity of the current emerging from the resistors is higher than a set value, a switch circuit (5) is closed allowing the current to pass distally A receiver (8) to communicate with an external controller is preferably included It is also not a necessary component if reducing the cost of the device need to be considered. The receiver communicates by radio frequency, infrared, ultrasound or any other means of telecommunications. The main proposed function is to provide an additional on/off switch (6) to the device. However, additional functions can be added to the telecommunication circuit like changing the value of the resistance and consequently the value of the intra-abdominal; pressure upon which the current passes distally beyond switch 1 (5). Additional circuits then needs to be added as necessary (like A/D, D/A converter).

Figure 2A:
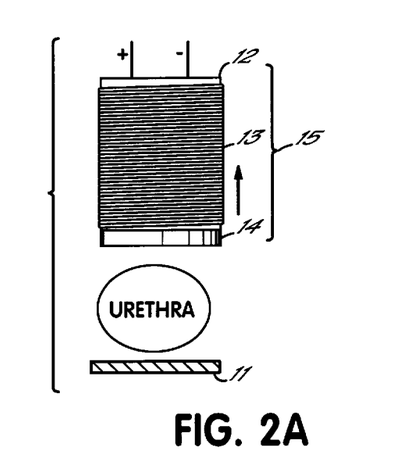
FIG. 2A is a side view of a controller device of the invention with normal intra-abdominal pressure and FIG. 2B is a similar view with increased intra-abdominal pressure.
Figure 2B:
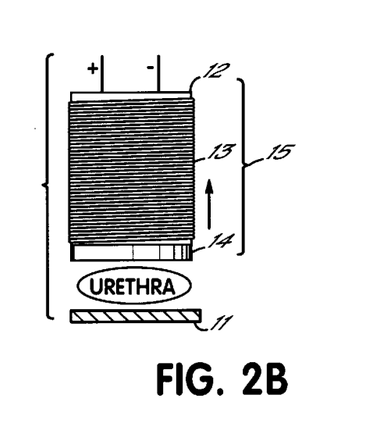

When the current passes distally, as occurs when intra-abdominal pressure rises, it reaches the controller device FIG. 2. The current produces magnetic field pulling a metal part located above the urethra to a basal plate located under the urethra, causing compression of the urethra and prevention of urine flow.

Figure 3:
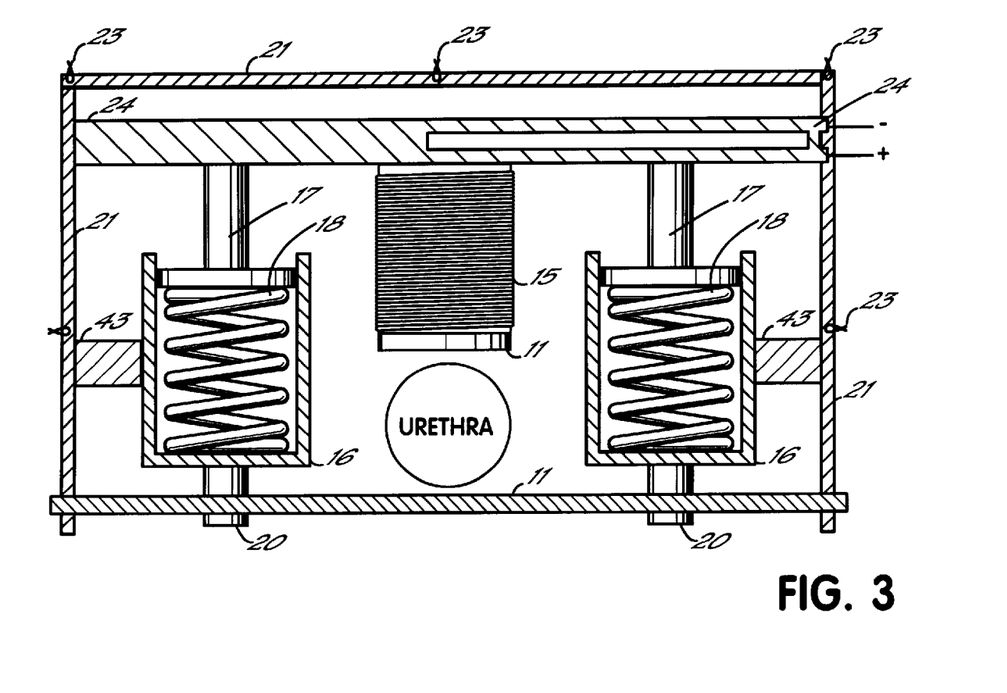
FIG. 3 is a side cross-sectional view of an embodiment of a controller device of the invention.

FIG. 3 illustrates the preferred embodiments of the controller device type A.

Figure 7:
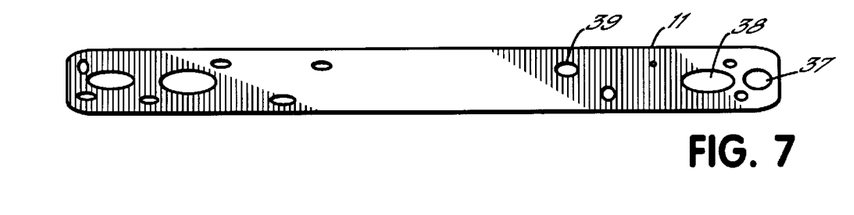
FIG. 7 is a schematic view of a basal plate for use in accordance with the principles of the present invention.

This device comprises a basal plate 11, best illustrated in FIG. 7, an envelope or a frame 21, a sliding bar 19 with a non- friction or low friction ends 24 moving up or down on track on the side wall of the envelope 21, barrels 16 with its plungers 17 and spring(s) 18 inside the barrels and an electromagnetic bar 15 attached to the sliding bar 19.

The basal plate 11 is placed between the urethra and the vaginal wall by a dilatation technique.

A set of different sizes of dilators are provided with the device to allow placement of the basal plate without the traditional surgical sharp dissection.

This set comprises an IV catheter, a guiding wire and dilators. The IV catheter is first passed between the urethra and the vaginal wall, its introducing needle is then removed and a guiding wire is passed through the catheter. The catheter is then removed leaving the guiding wire underneath the urethra. The smallest dilator is then passed over the wire and then removed. A second larger dilator is then passed over the wire and removed and so on, until the largest dilator is passed whose distal lumen allow the basal plate to pass through its largest diameter. The wire is then removed and the basal plate is then passed within the largest dilator and pulled from the other side of the urethra. The dilator is then removed leaving the basal plate under the urethra.

The basal plate as shown in FIG. 7 has two large holes on each side to allow the leg of the barrel 20 to pass in the appropriate hole and the leg of the side wall of the envelope 21 to pass through the second hole. It also has multiple peripheral holes to allow securing the plate to the surrounding tissues.

The envelope and the barrel legs are connected to the basal plate by click mechanism provided on the legs or by screws or any connecting means. The barrels are held stable by these legs as well as by stabilizer 43 fixing it to the side wall of the envelope.

A sliding bar 19 slides on a track provided on the inside of the side walls of the envelope. The sliding is facilitated by wheels or any non-friction ends. The bar has two extensions forming the plungers 17 of the barrels 16, and a central extension forming the electromagnetic bar 15. This electromagnetic bar comprises a metal bar 13 with coiled wire 12 and cushion on its distal end to smoothen the pressure imposed on the urethra by the bar.

When the intra-abdominal pressure rises above a set value a current is passed to the device creating a magnetic field pulling the magnetic part towards the basal plate and compressing the urethra, therefore, preventing urine flow.

Figure 4:
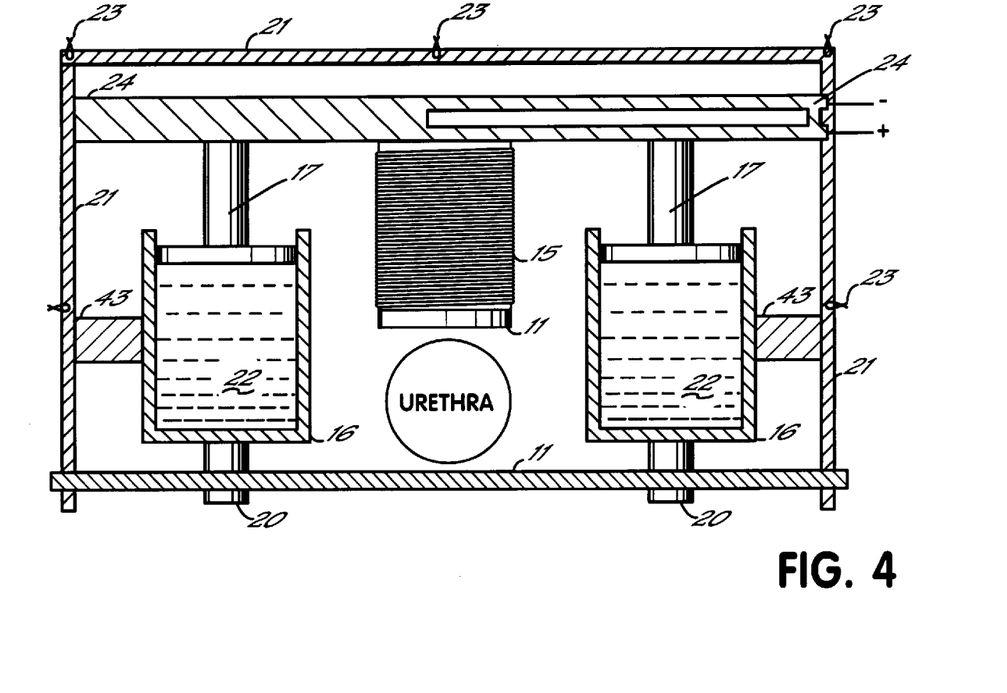
FIG. 4 is a side cross-sectional view of another embodiment of a controller device of the invention.

When the intra-abdominal pressure returns to normal the sliding bar returns to its resting position and removing the pressure on the urethra. The upward movement of the bar is provided by a spring 18 inside the barrel in type A or compressible gas or liquid 22 in the barrel as in type B.

A variety of different types of the above basic type can be made using the same principles. Some of those types are illustrated in FIG. 10, and FIG. 11.

Figure 10A:
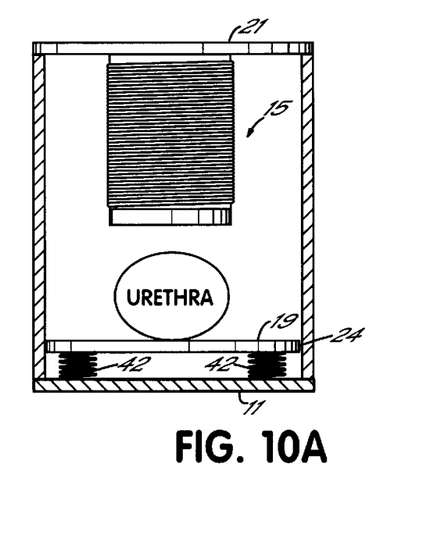
FIG. 10A is a side cross-sectional view of an alternative controller device of the invention with normal intra-abdominal pressure.
Figure 10B:
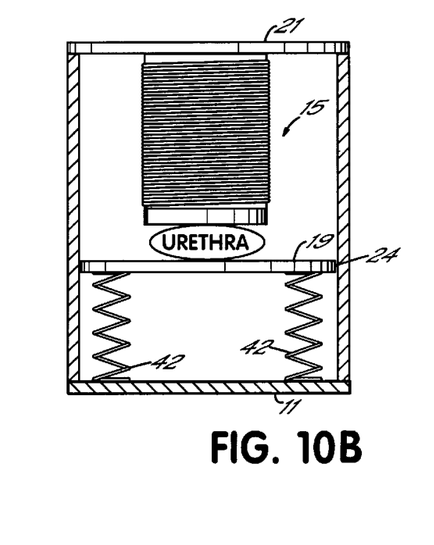
FIG. 10B is a similar view with increased intra-abdominal pressure.

FIG. 10 differs in that its sliding plate is placed with the basal plate underneath the urethra and attached to the basal plate by springs 42. The urethra in this type is compressed by the sliding bar under the urethra which pushes it upward towards the electromagnetic piece when a magnetic field is generated.

In this type of the device, the magnetic bar is fixed to the envelope, and it does not have barrels and plungers. The compression on the urethra is relieved by the springs placed between the sliding bar and the basal plate.

Figure 11A:
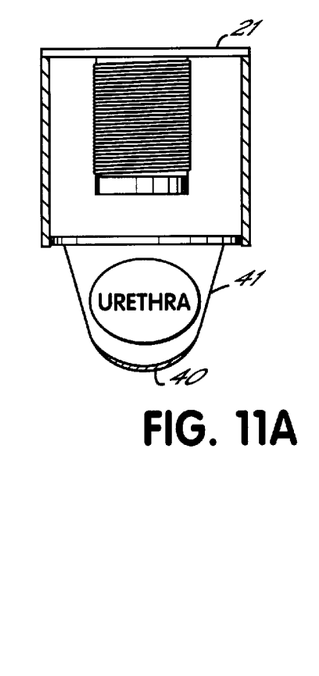
FIG. 11A is a side cross-sectional view of an alternative controller device of the invention with normal intra-abdominal pressure.
Figure 11B:
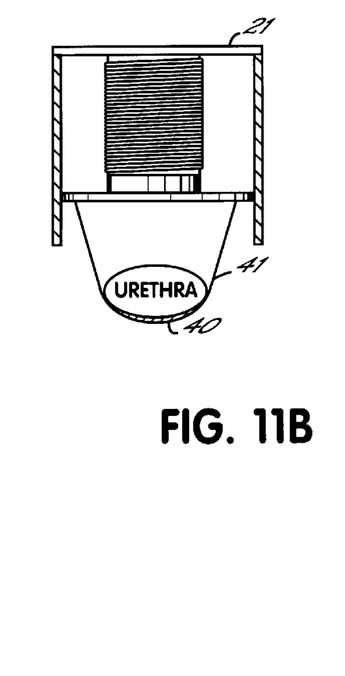
FIG. 11B is a similar view with increased intra-abdominal pressure.

FIG. 11 is also another form of the basic type in which the urethra is closed by a pulling sling 40 attached to the sliding bar by cords 41. This type of the device does not have a basal plate, instead it has the sling 40 passed underneath the urethra. This form, also, does not have barrels and plungers.

When the electromagnetic field is generated the sliding bar is pulled towards the magnetic bar pulling with it the cords and the sling changing the angle between the urethra and the bladder and preventing urine flow.

Although simpler to use, this type of the device may not be as reliable as the other forms in preventing the incontinence.

Figure 5:
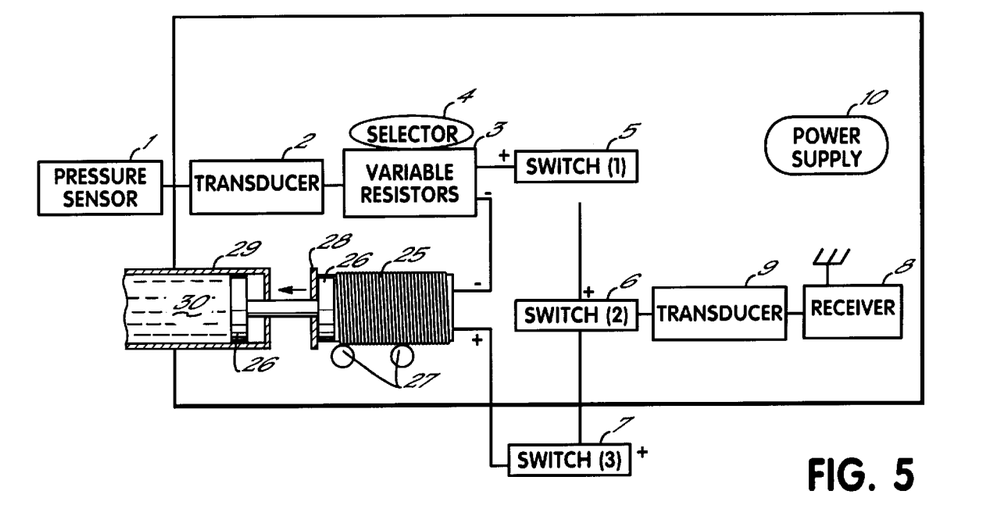
FIG. 5 is a schematic view of another embodiment of the invention.
Figure 6:
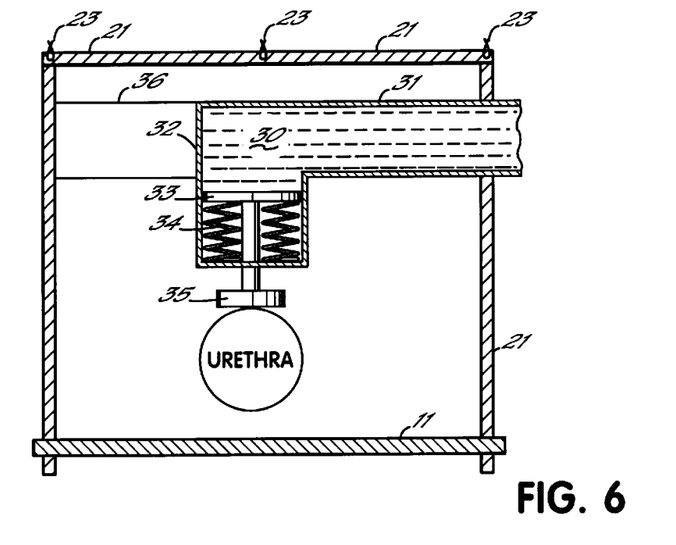
FIG. 6 is a side cross-sectional view of another embodiment of a controller device of the invention.

FIG. 5 and FIG. 6 illustrate type C of the device, the actuating and the controller device. Like type A and B of the device, the actuating device may or may not contain the variable resistors and the receiver circuits. It differs from them in that the electromagnetic bar, plunger and barrel are included in the actuating device rather than the controller device.

The electromagnetic bar 25 has wheels or sliders 27 that slide on a track on the inner wall of the envelope of the actuating device. Its distal end is continuous with a plunger 26 contained in a barrel 29 filled with a hydraulic fluid or gas 30.

The barrel has a metal plate 28 on its proximal end and both are fixed and not movable.

When the intra-abdominal pressure rises, an electromagnetic field is generated pulling the magnetic bar towards the metal bar 28 and pushing the plunger in causing the pressure inside the barrel to increase.

The increase in the barrel pressure is transmitted to the controller device type C shown in FIG. 6. A non-compliant tube tunneled under the skin connect the two parts of the device C filled with the same hydraulic gas or liquid.

Controller type C in FIG. 6 has also an envelope and a basal plate like type A,B. The above tube ends with a barrel 32 inside which a plunger 33 and spring(s) 34. The plunger has a cushion 35 on its distal end to smoothen the pressure on the urethra. The barrel is fixed in position by a holder 36.

When activated the urethra is compressed between the basal plate and the plunger. When the intra-abdominal pressure returns to normal spring 34 expand pushing the plunger upward relieving the urethral compression and pushing back the electromagnetic bar in the actuating device to its resting position. Spring 33 can be replaced by a compressible gas or fluid to achieve the same function.

Figure 9:
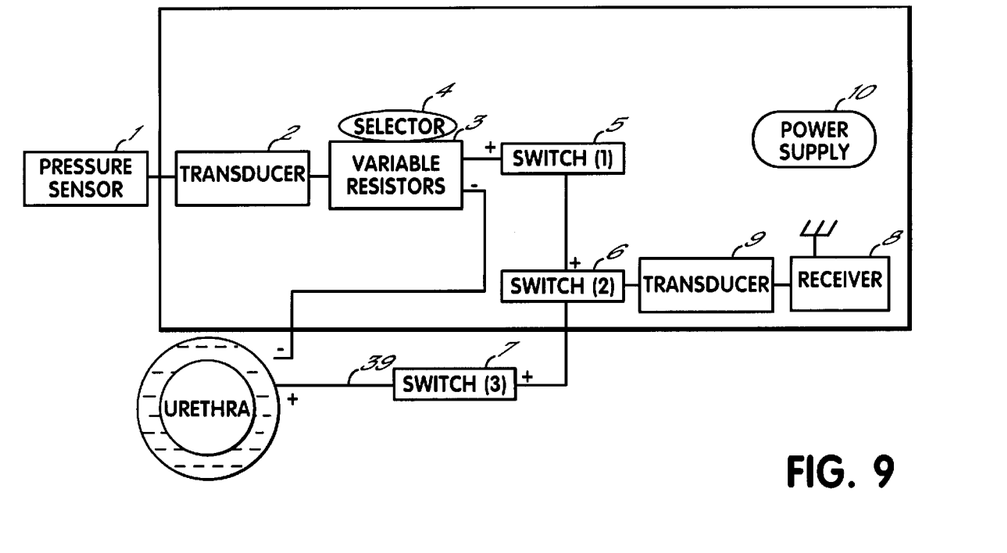
FIG. 9 is a schematic view of another embodiment of the invention.

Type D of the device is illustrated in FIG. 9. Like type A and B of the device, the actuating part may or may not comprise variable resistors and/or receiver circuits. The controller part is simply an electrode placed inside the wall of the urethral sphincter to enhance its contraction and tone during the increase in the inta-abdominal pressure.

The environmental placement of the device in human body is illustrated in FIG. 8 and FIG. 13. The actuating device and the pressure sensor are placed in the preferred site using the same incision. The sensor is placed in the abdominal cavity and the fascia is closed, then the actuating device is placed under the skin of the same incision and connected together by appropriate connectors.

The controller device is implanted around the urethra by a different skin incision and fixed to the surrounding tissues by appropriate stitches 23. The two parts of the device are then connected by the appropriate means tunneled under the skin.

A manual switch 7 is preferably implanted under the skin of the labia majora in female and the skin of the scrotum in males, but can be placed anywhere under the skin according to the preference of the operator.

When the patient wants to void, he has to turn the device off using either the manual switch under the skin or a remote control in case the device has the receiving circuits. When finishes, he or she has to turn it on again.

I claim:

1. An apparatus for preventing uncontrolled discharge of urinary fluid from a patient urethra, the device comprising:
    a pressure sensor operable for sensing intra-abdominal pressure when implanted in a patient and operable for generating a pressure signal in response to said sensed pressure;
    an actuating device operably coupled to the pressure sensor, the actuating device responsive for generating an electrical signal in response to the pressure signal;
    a controller operably coupled to the actuating device and configured for engaging a urethra to selectively compress the urethra and prevent incontinence, the controller comprising a plate adapted to be positioned on one side of the urethra and an element adapted to be positioned on another side of the urethra, the controller operable for varying the distance between the element and the plate in response to said electrical signal to compress the urethra therebetween so that incontinence is prevented when intra-abdominal pressure is experienced by a patient.

2. The apparatus of claim 1 wherein said pressure sensor has variable sensitivity for generating said pressure signal in response to sensed pressures of varying strength.

3. The apparatus of claim 1 wherein said actuating device comprises a transducer coupled to the pressure sensor for generating said electrical signal.

4. The apparatus of claim 3 wherein said actuating device comprises at least one variable resistor electrically coupled to the transducer, the variable resistor affecting the level of the electrical signal.

5. The apparatus of claim 3 wherein the actuating device further comprises a comparator switch coupled to the transducer, the comparator switch closing when said electrical signal is at a predetermined value so that the electrical signal is coupled to the controller.

6. The apparatus of claim 1 further comprising a control switch coupled between said pressure sensor and said controller, the control switch being selectively opened and closed to selectively uncouple the controller from the actuating device.

7. The apparatus of claim 6 wherein said control switch includes a remote control portion.

8. The apparatus of claim 1 wherein the controller includes a biasing device operably coupled to at least one of the element and the plate for biasing one of the element and the plate away from the other, the biasing device separating the element and the plate in the absence of said electrical signal for removing the compression of the urethra.

9. The apparatus of claim 8 wherein said biasing device includes a spring.

10. The apparatus of claim 8 wherein said biasing device includes a plunger and one of a gas and a liquid directed against the plunger.

11. The apparatus of claim 10 wherein said plunger compresses one of said gas and liquid when-the element moves toward the metal plate.

12. The apparatus of claim 1 wherein said controller plate is a metal plate and the element is an electromagnetic element, the electromagnetic element creating a magnetic field proximate the metal plate in response to the electrical signal for magnetically varying the distance between the electromagnetic element and the metal plate to compress the urethra.

13. The apparatus of claim 12 wherein said electromagnetic element is movable and the metal plate is fixed, the electro magnetic element moving toward the metal plate in response to the created magnetic field.

14. The apparatus of claim 12 wherein said electromagnetic element is fixed and the metal plate is movable, the metal plate moving toward the electro-magnetic element in response to the created magnetic field.

15. The apparatus of claim 1 wherein said element includes a plunger coupled to one of a gas and a liquid, the apparatus further comprising a device for compressing said one of a gas and a liquid for moving the plunger and varying the distance between the plate and the plunger to compress the urethra.

16. The apparatus of claim 15 wherein said compressing device includes a metal plate and an electromagnetic element coupled to a second plunger, the second plunger coupled to the one of a gas and liquid and the electromagnetic element creating a magnetic field proximate the metal plate in response to the electrical signal for magnetically moving the electromagnetic element toward the metal plate to move the second plunger and compress the one of a gas and a liquid.

17. The apparatus of claim 1 wherein said element includes a cushion on a portion thereof for cushioning the compression of the urethra between the element and the plate.

18. An apparatus for preventing uncontrolled discharge of urinary fluid from a patient urethra, the device comprising:

a pressure sensor operable for sensing intra-abdominal pressure when implanted in a patient and operable for generating a pressure signal in response to said sensed pressure;

an actuating device operably coupled to the pressure sensor, the actuating device responsive for generating an electrical signal in response to the pressure signal;

a controller operably coupled to the actuating device and configured for engaging a urethra to selectively compress the urethra and prevent incontinence, the controller comprising a sling adapted to be positioned on one side of the urethra and a movable metal element coupled to the sling, and further comprising an electromagnetic element positioned proximate the metal element, the electromagnetic element creating a magnetic field proximate the metal element in response to the electrical signal for magnetically moving the metal element and thereby directing the sling against the urethra to compress the urethra so that incontinence is prevented when intra-abdominal pressure is experienced by a patient.

19. The apparatus of claim 18 further comprising cords suspending the sling from the movable metal element.

* * * * *